US010849215B2

(12) United States Patent
Van Abeelen et al.

(10) Patent No.: US 10,849,215 B2
(45) Date of Patent: Nov. 24, 2020

(54) COLD PLASMA DEVICE FOR TREATING A SURFACE

(71) Applicant: KONINKLIJKE PHILIPS N.V., Eindhoven (NL)

(72) Inventors: Frank Anton Van Abeelen, Eindhoven (NL); Eduard Gerard Marie Pelssers, Eindhoven (NL); Yannyk Parulian Julian Bourquin, Eindhoven (NL); Achim Hilgers, Eindhoven (NL); Roland Cornelis Martinus Vulders, Eindhoven (NL); Lili-Marjan Brockhuis, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 158 days.

(21) Appl. No.: 16/086,456

(22) PCT Filed: Mar. 21, 2017

(86) PCT No.: PCT/EP2017/056602
§ 371 (c)(1),
(2) Date: Sep. 19, 2018

(87) PCT Pub. No.: WO2017/162614
PCT Pub. Date: Sep. 28, 2017

(65) Prior Publication Data
US 2019/0104605 A1   Apr. 4, 2019

(30) Foreign Application Priority Data
Mar. 22, 2016   (EP) .................................... 16161743

(51) Int. Cl.
H05H 1/24 (2006.01)
A61L 2/14 (2006.01)
(Continued)

(52) U.S. Cl.
CPC ......... *H05H 1/2406* (2013.01); *A61B 18/042* (2013.01); *A61L 2/0011* (2013.01);
(Continued)

(58) Field of Classification Search
CPC ......... H05H 1/2406; H05H 2001/2412; H05H 2240/10; H05H 2240/20; H05H 2245/122;
(Continued)

(56) References Cited

U.S. PATENT DOCUMENTS 8,267,884 B1 *  9/2012  Hicks ................... A61B 18/042
                                                           315/111.21
8,557,187 B2   10/2013  Ehlbeck
(Continued)

FOREIGN PATENT DOCUMENTS

CN      203869182 U      10/2014
DE      102009002278 A1  10/2010
(Continued)

OTHER PUBLICATIONS

I.E. Idelchik, "Flow Resistance", Hemisphere Publishing Corp., New York (1988).

*Primary Examiner* — Xiuyu Tai

(57) ABSTRACT

The present application relates to a cold plasma device (13) for treating a surface (6) with cold plasma. The device (13) has a cold plasma generator (14) adapted to generate cold plasma that produces reactive species for treating the surface (6). The device (13) also includes a treatment head (5) that is positionable relative to the surface (6) such that the reactive species are imparted toward the surface (6) during treatment. The device (13) is also provided with an air flow generator (8) to generate an air flow over the surface (6) and a controller (9) configured to control operation of the air flow generator (8) to generate an air flow over the surface (6)

(Continued)

after the treatment has been completed such that remaining by-products of the cold plasma are dissipated.

20 Claims, 4 Drawing Sheets

(51) Int. Cl.
*A61L 2/00* (2006.01)
*A61B 18/04* (2006.01)
*A61B 18/00* (2006.01)
*A61B 90/00* (2016.01)

(52) U.S. Cl.
CPC ....... *A61L 2/14* (2013.01); *A61B 2018/00017* (2013.01); *A61B 2018/00583* (2013.01); *A61B 2090/065* (2016.02); *A61L 2202/11* (2013.01); *A61L 2202/14* (2013.01); *H05H 2001/2412* (2013.01); *H05H 2240/10* (2013.01); *H05H 2240/20* (2013.01); *H05H 2245/122* (2013.01); *H05H 2245/123* (2013.01); *H05H 2245/1225* (2013.01); *H05H 2277/10* (2013.01); *H05H 2277/14* (2013.01)

(58) Field of Classification Search
CPC ..... H05H 2245/1225; H05H 2245/123; H05H 2277/10; H05H 2277/14; H05H 1/48; H05H 2001/481; H05H 2245/121; A61B 18/042; A61B 2090/065; A61B 2018/00017; A61B 2018/00583; A61B 2018/00744; A61B 2018/00898; A61B 34/30; A61B 2562/0257; A61B 2018/00642; A61B 2018/00452; A61B 2018/00023; A61L 2/0011; A61L 2/14; A61L 2202/11; A61L 2202/14; A61L 9/22; B03C 3/41; B03C 3/011; B03C 3/38; B03C 3/68; F24F 3/166; F24F 2003/1682; Y02A 50/22; H02M 7/003

See application file for complete search history.

(56) References Cited

U.S. PATENT DOCUMENTS

| 9,034,270 | B2 | 5/2015 | Kobayashi |
| 2009/0206062 | A1 | 8/2009 | Kuo |
| 2013/0345620 | A1 | 12/2013 | Zemel |
| 2014/0147333 | A1 | 5/2014 | Morfill |

FOREIGN PATENT DOCUMENTS

| JP | 2014136045 | A | 7/2014 |
| WO | 2004014439 | A2 | 2/2004 |
| WO | 2006003382 | A1 | 1/2006 |
| WO | 2010094304 | A1 | 8/2010 |
| WO | 2010109160 | A1 | 9/2010 |
| WO | 2014167520 | A1 | 10/2014 |

* cited by examiner

COLD PLASMA DEVICE FOR TREATING A SURFACE

This application is the U.S. National Phase application under 35 U.S.C. § 371 of International Application No. PCT/EP2017/056602, filed on Mar. 21, 2017, which claims the benefit of International Application No. 16161743.6 filed on Mar. 22, 2016. These applications are hereby incorporated by reference herein.

FIELD OF THE INVENTION

This disclosure relates to a cold plasma device for treating a surface with cold plasma.

BACKGROUND OF THE INVENTION

It is known to use a cold plasma device to disinfect objects. A cold atmospheric plasma generates reactive oxygen and nitrogen species that are biologically active and able to inactivate bacteria.

In particular, US20090206062 discloses a hand held plasma spray device that generates a cold atmospheric plasma and uses a fan to blow the resultant reactive species out of a nozzle and towards an object to be treated.

It is to be noted that US20130345620 discloses a device for treating a skin surface with cold plasma. The device according to this disclosure may comprise a gas flow during the application of the cold plasma to assist the treatment.

It is further to be noted that DE102009002278 discloses a device for treating skin using a combination of ultrasound and cold plasma in which the treatment head defines an enclosed volume between the skin and the cold plasma generating electrodes which volume might be filled with a fluid either during or after the plasma treatment.

Such cold plasma treatments create by-products, for example the remaining reactive species—e.g. ozone and nitrogen dioxide. These by-products may be undesirable.

SUMMARY OF THE INVENTION

It is an object of the invention to provide a cold plasma device for treating a surface which substantially alleviates or overcomes one or more of the problems mentioned above.

The invention is defined by the independent claims. The dependent claims define advantageous embodiments.

According to the present invention, there is provided a cold plasma device for treating a surface with cold plasma, the device comprising:

a cold plasma generator adapted to generate cold plasma that produces reactive species for treating said surface;

a treatment head positionable relative to said surface such that said reactive species are imparted toward said surface during treatment;

an air flow generator to generate an air flow over said surface; and, a controller configured to control operation of the air flow generator to generate an air flow over said surface after said treatment has been completed such that remaining by-products of the cold plasma are dissipated.

In addition to dissipating the by-products, the air flow will also disperse any odorous volatiles, in particular those produced by bacteria on a skin surface.

Completion of treatment may occur when the cold plasma device is moved partially or completely away from a treatment surface, as detected by, for example, a proximity sensor, or when it is moved out of contact with the treatment surface, as detected by, for example, a contact sensor, even if the cold plasma generator is still operational. Alternatively, completion of treatment may occur when the cold plasma generator is switched off.

If the cold plasma device were used to inactivate bacteria on skin (for example a deodorising device), then the air flow will dissipate remaining odorous by-products of the cold plasma.

The controller may be configured to control the air flow generator to generate an air flow over said surface only after said treatment has been completed.

In this way, the cold plasma treatment takes place without an air flow, which may be beneficial, but an air flow is provided to dissipate remaining by-products of the cold plasma treatment after the treatment has been completed.

The controller may be configured to control the air flow generator to generate an air flow over said surface during said treatment.

In this example, an air flow may be beneficial during the cold plasma treatment (for example pushing reactive species toward the surface), and after the cold plasma generator is switched off the air flow acts to dissipate remaining by-products of the cold plasma and any other odorous volatiles.

The controller may be configured to alter an operating characteristic of the air flow generator after said treatment has been completed.

Therefore, an air flow can be generated during the treatment to help the cold plasma treatment, and the air flow after the treatment has been completed will dissipate remaining by-products of the cold plasma.

The controller may be configured to increase the power of the air flow generator when said treatment has been completed.

For example, during the treatment there may be an air flow that urges reactive species toward the surface, and after the treatment has been completed the rate of the air flow may be increased to dissipate remaining by-products of the cold plasma. Therefore, the different air flows are used to help the cold plasma treatment and to dissipate any remaining by-products.

The controller may be configured to reverse the direction of the air flow generator after said treatment has been completed.

For example, the controller may be configured to control the air flow generator to generate an air flow toward the surface during treatment, and to control the air flow generator to generate an air flow away from the surface after said treatment has been completed.

In this way, during treatment the air flow will urge reactive species towards the skin, but after the treatment has been completed the air flow will suck remaining by-products of the cold plasma away from the surface to dissipate them.

The cold plasma device may further comprise a sensor adapted to detect when the treatment head is positioned in contact with or proximate to said surface, the controller being configured to switch on the cold plasma generator in response to a signal from the sensor.

In this way, the cold plasma device may only be switched on when the treatment head is in an appropriate position relative to the surface.

The cold plasma device may further comprise a sensor adapted to detect when the treatment head is positioned in contact with or proximate to said surface, and the controller may be configured to control operation of the air flow generator to generate an air flow over said surface after the sensor detects that the treatment head has been removed from said surface.

In this way, it is possible to control the air flow generator differently depending on whether the treatment head is positioned against the surface, is proximate to the surface, or is spaced more significantly from the surface. In one example, the air flow generator generates an air flow over the surface immediately after the treatment head has been removed from the surface. In this way, the by-products are dissipated while the cold plasma device is still proximate to the surface.

The controller may be configured to control operation of the air flow generator to generate an air flow over said surface after said cold plasma generator has been switched off.

In this way, the air flow is generated to disperse by-products after the cold plasma treatment has been completed.

In another example, the controller is configured to control operation of the air flow generator to generate an air flow over said surface after said cold plasma generator has been switched off and after the sensor detects that the treatment head has been removed from said surface.

Therefore, the controller may determine when the treatment has been completed in three ways:
when the treatment head has been removed from the surface;
when the cold plasma generator has been switched off; or
when the cold plasma generator has been switched off and when the treatment head has been removed from the surface.

The air flow generator may be adapted to generate a flow of air towards said surface.

Air flow towards the surface will dissipate remaining by-products of the cold plasma by blowing them away from the surface.

The air flow generator may be adapted to generate a flow of air away from said surface.

Air flow away from the surface will dissipate remaining by-products of the cold plasma by sucking them away from the surface.

The cold plasma device may further comprise a filter arranged to filter said air flow.

The filter may be positioned to remove by-products from the air flow. In this way, any by-products are removed from the vicinity of the surface. Instead, or in addition to a filter, the cold plasma device may comprise a reservoir to store the air for a period long enough for the by-products to decay.

The cold plasma generator may be mounted in the treatment head, and the treatment head may be adapted such that during treatment the cold plasma generator is proximate to, and spaced from, said surface.

Such an arrangement is preferable because the spacing allows the reactive species to reach the treated surface more uniformly.

The cold plasma generator may comprise an aperture or a number of apertures through which the air flow generated by the air flow generator can pass.

In this way, the air flow is directed through the area in which the cold plasma is generated, which is effective for dissipating remaining by-products of the cold plasma.

The cold plasma device may further comprise a duct arranged to guide the air flow generated by the air flow generator, and the duct may bypasses the cold plasma generator and may comprise an aperture disposed within the treatment head. It is further possible to provide a second aperture in the handle of the device so that air can be sucked in through the second aperture and mixed with the air sucked in via the treatment head to dilute the air sucked in via the treatment head.

In this way, the air flow can act to displace or suck the remaining by-products of the cold plasma, effectively dissipating them. By ducting the air flow, it is accelerated and so the by-products are removed more quickly from the treatment area. A duct that bypasses the cold plasma generator will also protect internal parts, such as the electronics, of the device from reactive by-products. The controller may be configured to control the air flow generator such that an air flow over said surface is maintained for a fixed time period after said cold plasma generator has been switched off.

This provides a simple solution for determining when the air flow generator should be switched off after the cold plasma generator has been switched off. A fixed time period will allow for sufficient dissipation of the remaining by-products without the user having to manually switch off the air flow generator.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
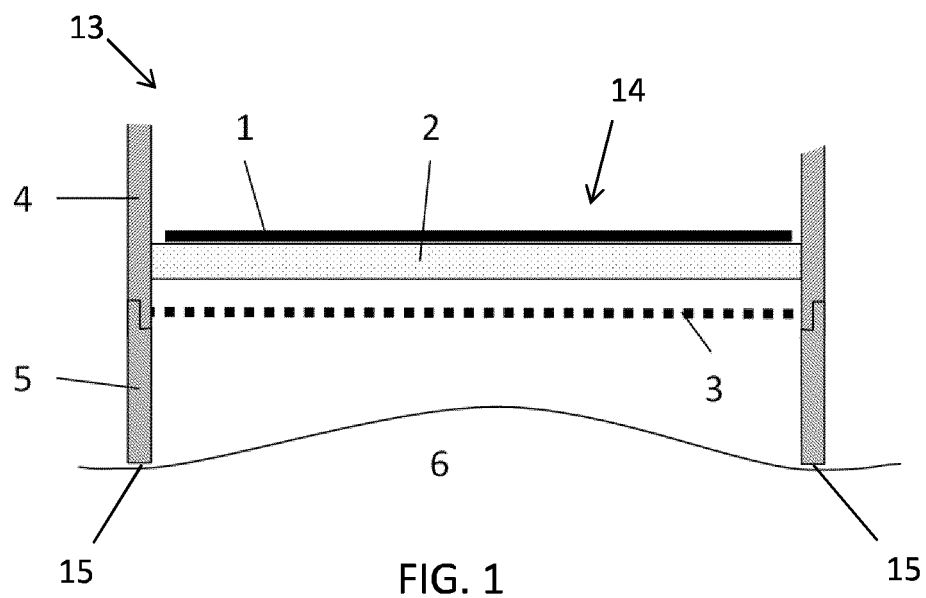
FIG. 1 shows a cross-section of a cold plasma device for treating a surface in the region of a cold plasma generator, the cold plasma device is in an operational position against a user's skin.

The cold plasma device 13 of FIG. 1 comprises a housing 4 that holds a cold plasma generator 14. The cold plasma device 13 further includes a spacer element 5 that, when the cold plasma device 13 is in use, acts to space the cold plasma generator 14 from the surface 6 being treated. The spacer element 5 effectively constitutes a treatment head that is placed against the surface 6 during use of the device 13. In alternative examples, the spacer element 5 may not be placed in contact with the surface 6 during use of the device 13, but rather held a distance from the surface 6.

The term cold plasma is used to describe plasmas at an ion temperature that is less than about 100 degrees Celsius, and is therefore suitable for use on and around people, particularly on skin. The ion temperature is the temperature of the ions and the neutral molecules after being thermalized. The ionization level is about one molecule in one million. Therefore by collisions with other molecules ions reach thermal equilibrium, i.e. they are thermalized. In the treatment of skin, the temperature rise will be at maximum a few degrees. However, for cleaning other surfaces more energy can be used and the temperature can reach 100 degrees.

The cold plasma generator 14 of the example of FIG. 1 comprises a first electrode 1, a second electrode 3, and a dielectric material 2 disposed between the first and second electrodes 1, 3. As shown in FIG. 1, the cold plasma generator 14 extends across the housing 4 so that it is substantially parallel with an end face 15 of the spacer element 5. In this way, the cold plasma generator 14, particularly the second electrode 3, is substantially evenly spaced from the surface 6 during use (depending on the characteristics of the surface 6 being treated). When the device is being used to treat skin, doming of the skin may occur but the second electrode 3 will remain substantially parallel to a plane that is characterised by the average surface normal.

The cold plasma generator 14 is connected to a power supply (17, see FIG. 2) within the device 13 such that a voltage is generated across the first and second electrodes 1, 3. The dielectric material 2 acts to insulate the first electrode 1 from the second electrode 3.

The above-described structure of the cold plasma generator is termed a dielectric barrier discharge cold plasma generator. A pulsed or alternating voltage with amplitude of several kilovolts is applied across the first electrode 1 and the second electrode 3. The dielectric material 2 prevents direct discharge between the first electrode 1 and the second electrode 3. Instead, filaments (micro-discharges) are generated between the dielectric material 2 and the second electrode 3. These filaments are created by the ionisation of molecules present between the first and second electrodes 1, 3, for example nitrogen molecules within the air, caused by the high voltage. This ionisation process releases electrons which collide with, and ionise, other molecules present between the first and second electrodes 1, 3.

In this way, ionised reactive species are generated from the air between the first and second electrodes 1, 3. The reactive species may include nitrogen oxides, atomic oxygen, ozone, hydroxyl, reactive oxygen species and reactive nitrogen species. These reactive species are chemically reactive and can inactivate bacteria, and are thus useful for treating surfaces.

The skilled person will appreciate that the cold plasma generator 14 may have an alternative structure. For example, US20140147333 describes two alternative arrangements of cold plasma generators. A first example is a surface micro discharge cold plasma generator in which the dielectric material fills the entire space between the first and second electrodes. Another example is a self-sterilizing surface cold plasma generator, in which the first and second electrodes are embedded in dielectric material, and so the filaments are emitted from a surface of the dielectric material.

Moreover, the skilled person will appreciate that cold plasma can be generated within a fluid that is not air, as described above. For example, other gasses can be provided to the space between the dielectric material 2 and the second electrode 3, and these gasses would be ionised by the cold plasma generator 14 and create reactive species. Such other gasses could be provided from a compressed gas source.

In the examples of FIG. 2 to FIG. 7, the cold plasma device 13 has a cold plasma generator of any of the types described above, and further comprises an air flow generator 8, for example a fan. The air flow generator 8 is adapted to generate an air flow over the surface 6 being treated during use of the cold plasma device 13. A controller 9 is provided to control operation of the air flow generator 8.

In one example, the controller 9 is configured to control operation of the air flow generator 8 to generate air flow over the surface 6 after treatment has been completed, to dissipate odorous by-products of the cold plasma. The air flow created by the air flow generator 8 may be towards the surface 6 or away from the surface 6.

Figure 2:
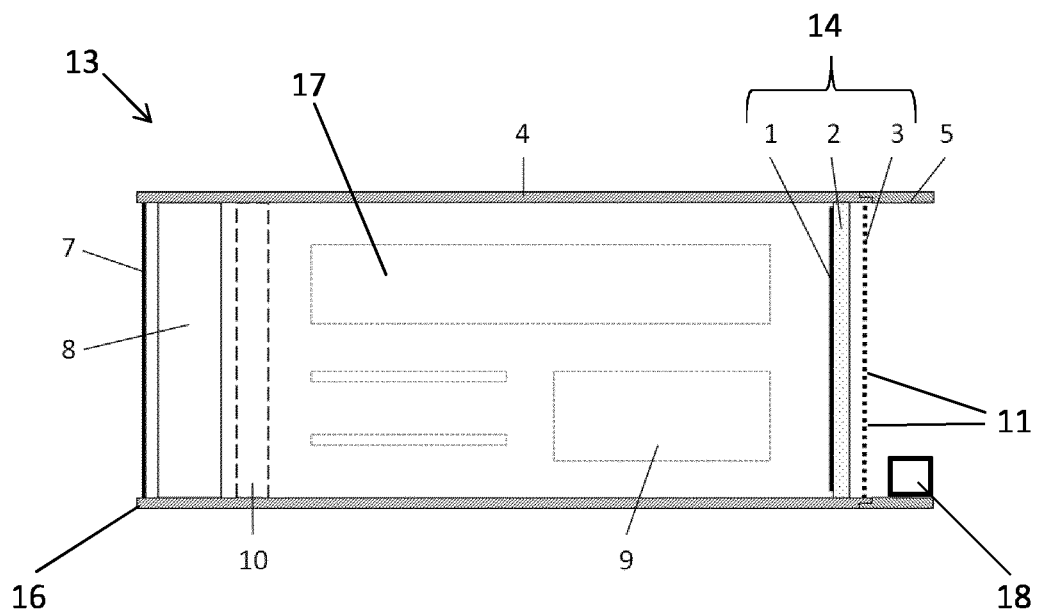
FIG. 2 shows a schematic view of a first example cold plasma device for treating a surface, showing a cold plasma generator for treating a surface and an air flow generator.

In the example of FIG. 2, the air flow generator is a fan 8. As shown, the cold plasma device 13 includes a housing 4, spacer element 5 and cold plasma generator 14 as previously described with reference to FIG. 1.

The fan 8 is located at an end 16 of the housing 4 which is opposite to the spacer element 5, and that end 16 of the housing is provided with an inlet 7 to permit air to flow from the fan 8 through the end 16 of the housing 4 to atmosphere (or vice versa). The end 16 of the housing 4 adjacent to the fan 8 may be provided with a protective grid having multiple inlets 7 that permit air flow while protecting the fan 8.

Between the fan 8 and the cold plasma generator 14 are located other components of the cold plasma device, for example the controller 9 and a power supply 17. In this embodiment, the housing 4 acts a duct for the air flow generated by the fan 8. In particular, the fan 8 generates an air flow from/to the surface 6 being treated via the housing 4 and spacer element 5.

Optionally, as shown in FIG. 2 the cold plasma device 13 may also include a filter 10. In this example, the filter 10 is disposed between the fan 8 and the surface 6 being treated. Therefore, if the fan 8 is operated to generate an air flow away from the surface 6, the air flow is filtered by the filter 10 before reaching the fan 8 to remove any by-products of the cold plasma being carried in the air flow. In alternative arrangements, a filter 10 may be provided on an opposite side of the fan 8 to that shown in FIG. 2, such that the fan 8 is disposed between the filter 10 and the surface 6 being treated. In this way, air flow away from the surface 6 is filtered after passing through the fan 8 to remove any by-products of the cold plasma being carried in the air flow, and air flow towards the surface 6 is filtered before passing through the fan 8 so that clean air is provided to dissipate the by-products of the cold plasma.

The filter may comprise a fibrous material that traps constituents of the air flow, or it may comprise an absorbent or adsorbent substance to absorb or adsorb, respectively, constituents of the air flow. In other embodiments, the filter may include active ingredients, such as activated carbon, to filter the air flow through chemical reactions. The filter may also encompass other techniques such as photocatalytic oxidation, (PCO), UV radiation, and dry or wet scrubbing.

In the example of FIG. 2, the air flow generated by the fan 8 passes through the cold plasma generator 14.

As explained previously, in the illustrated example the cold plasma generator 14 comprises first and second electrodes 1, 3 and a dielectric material 2 disposed in between. In other embodiments the cold plasma generator 14 may comprise different arrangements of the first and second electrodes and dielectric material, as previously explained.

In this embodiment, the components 1, 2, 3 of the cold plasma generator 14 are provided with passages 11 through which the air flow can pass. In this way, air flow generated by the fan 8 can reach the surface 6 being treated.

In the example of FIG. 2, the first and second electrodes 1, 3 of the cold plasma generator 14 may each comprise a mesh that has a plurality of openings 11 through which air flow can pass. The dielectric material 2 may also have openings distributed over its surface.

Figure 3:
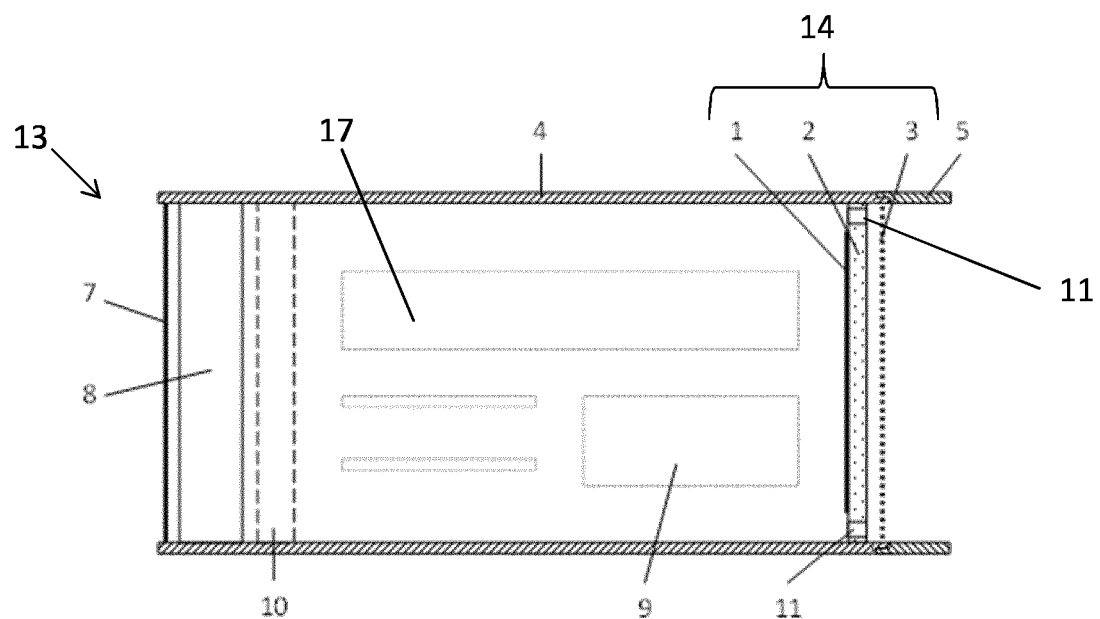
FIG. 3 shows a schematic view of a second example cold plasma device for treating a surface, showing a cold plasma generator for treating a surface and an air flow generator.

FIG. 3 shows an example similar to the example of FIG. 2. In this example the cold plasma device 13 includes a housing 4, a cold plasma generator 14, a fan 8 and an optional filter 10. However, in this example at least one component 1, 2, 3 of the cold plasma generator 14 is provided with a plurality of openings 11 arranged around a peripheral edge of the cold plasma generator 14 within the housing 4. This is more clearly shown in FIG. 4.

Figure 4:
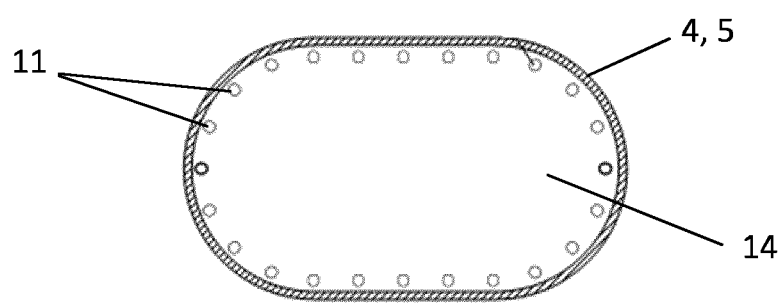
FIG. 4 shows an end view of the cold plasma device of FIG. 3.

In one example, illustrated in FIG. 3, the second electrode 3, which is disposed closest to the surface 6 during use, comprises a mesh that allows air flow to pass through it, while the first electrode 1 and the dielectric material 2 are provided with openings 11 arranged around a peripheral edge of the cold plasma generator 14, in the positions shown in FIG. 4. The electrode 1 covers a slightly smaller area than the dielectric material 2 so that the dielectric material 2 overlaps the electrode 1 around its periphery.

In another example, the second electrode 3, disposed closest to the surface during use, comprises openings 11 arranged around a peripheral edge of the cold plasma generator 14, similar to those shown in FIG. 4, while the first electrode 1 comprises a mesh that permits air to flow through it. The dielectric material 2 may comprise openings 11 arranged around a peripheral edge of the cold plasma generator 14 similar to those shown in FIG. 4.

In all of these examples, air can flow through the cold plasma generator 14.

By providing openings 11 around the peripheral edge of the cold plasma generator 14, as illustrated in FIG. 4, the function of the components 1, 2, 3 of the cold plasma generator 14 is not adversely affected. In particular, it is important for the functioning of the cold plasma generator 14 that the dielectric material 2 provides an insulative barrier between the first and second electrodes 1, 3. Arranging openings 11 around the peripheral edge of the dielectric material 2, in the positions shown in FIG. 4, is preferable as it has least effect on the insulative function of the dielectric material 2 and there is still a uniform plasma source in a central part of the treatment head.

Figure 5:
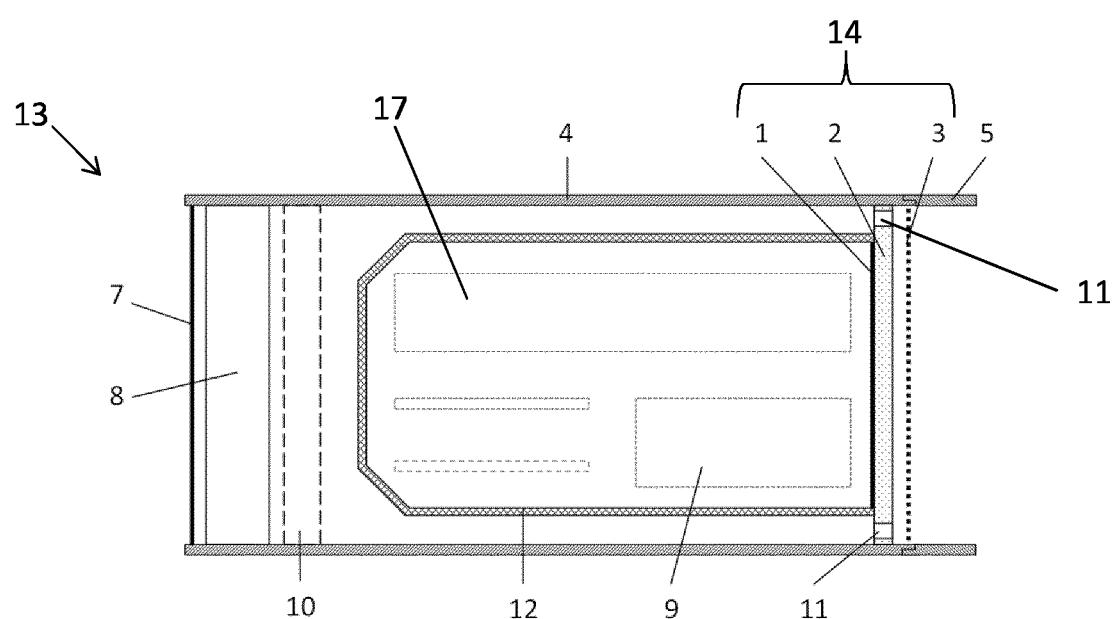
FIG. 5 shows a schematic view of a third example cold plasma device for treating a surface, showing a cold plasma generator for treating a surface and an air flow generator.

In the example illustrated in FIG. 5, the cold plasma device 13 is further provided with an internal casing 12 that surrounds at least some of the internal components of the cold plasma device 13 (e.g. the controller 9 and the power supply 17). The internal casing 12 defines a duct for the air flow that circumvents these internal components. As shown, the internal casing 12 defines a duct that passes from the inlet 7, past the fan 8, through the optional filter 10, around the internal components to the cold plasma generator 14.

In this example, the duct is arranged such that air flow is directly provided to a peripheral region of the cold plasma generator 14, where openings 11 may be provided in a similar pattern to that shown in FIG. 4. However, it will be appreciated that the internal casing 12 can have a different shape such that the duct is aligned with openings 11 in other positions on the cold plasma generator 14. Or in the case of the electrodes 1, 3 of the cold plasma generator 14 comprising meshes, the duct may provide air flow directly to the entire surface of the cold plasma generator 14.

Figure 6:
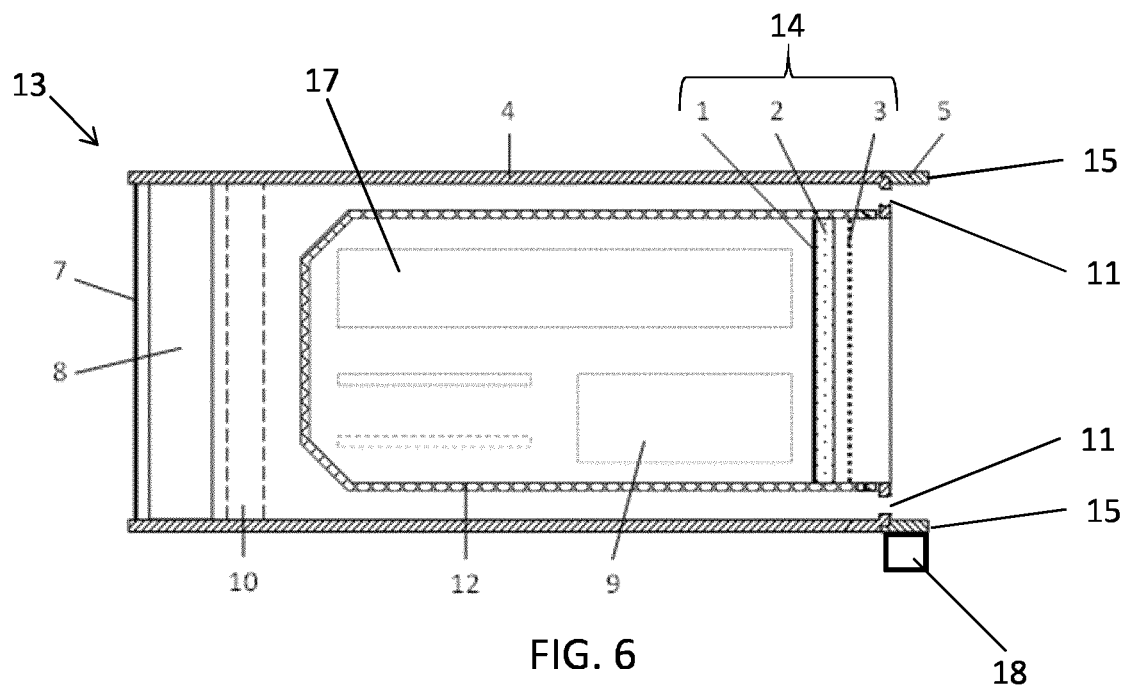
FIG. 6 shows a schematic view of a fourth example cold plasma device for treating a surface, showing a cold plasma generator for treating a surface and an air flow generator; and, FIG. 7 shows a schematic view of a fifth example cold plasma device for treating a surface, showing a cold plasma generator for treating a surface and an air flow generator.
Figure 7:
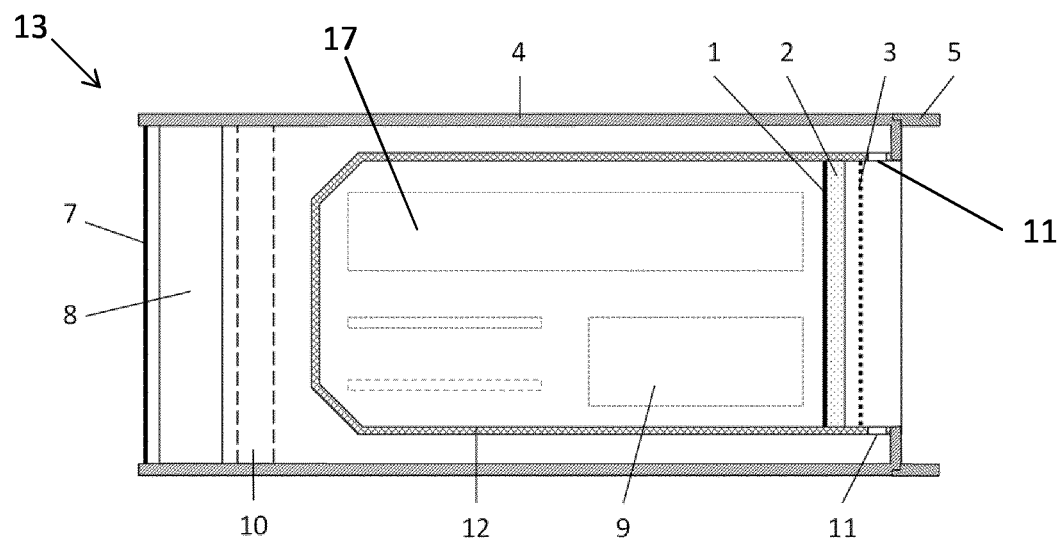

In the examples of FIG. 6 and FIG. 7, the cold plasma device 13 is arranged such that the air flow does not pass directly through the cold plasma generator 14, but rather around the cold plasma generator 14.

As illustrated in FIG. 6 and FIG. 7, the cold plasma device 13 of these examples is provided with an internal casing 12 that defines a duct, similar to that of FIG. 5. However, in these examples the duct extends past the peripheral edge of the cold plasma generator 14 so that the air flow bypasses the cold plasma generator 14. One or more openings 11 are provided in the end of the duct, in this example between the internal casing 12 and the spacer element 5, so that air can flow between the surface 6 being treated and the fan 8.

As shown in FIG. 6 and FIG. 7, the cold plasma generator 14 is mounted to the internal casing 12 such that the duct defined by the internal casing 12 can bypass the cold plasma generator 14.

In the example of FIG. 6, the openings 11 at the end of the duct are directed towards the end 15 of the spacer element 5, and therefore towards the surface 6 during treatment.

In the example of FIG. 7, the openings 11 in the end of the duct are directed across the surface of the cold plasma generator 14, so that the air flows in a direction across the surface 6.

As mentioned previously, the controller 9 is configured to control operation of the air flow generator 8 such that the air flow generator 8 generates an air flow over the surface 6 being treated after the treatment has been completed.

In the above examples the air flow generator 8 has been described as a fan. However, the skilled person will understand that the air flow generator 8 may alternatively be a blower, a displacement pump, a screw pump, a bladeless fan, vacuum or any other component that can create an air flow.

In each of the examples of FIG. 1 to FIG. 7, the controller 9 can be configured to operate the air flow generator 8 such that an air flow is generated over the surface 6 (in either direction) for a fixed period of time after the treatment has been completed. In this case, the air flow generator 8 is switched on for a fixed period of time after the treatment has been completed to dissipate by-products of the cold plasma.

In these examples, the controller 9 may be configured such that the air flow generator 8 only generates an air flow over the surface 6 after treatment has been completed. In this case, during treatment the air flow generator 8 is switched off.

In this way, the air flow will not disturb the cold plasma treatment process by dissipating the reactive species before they have had a chance to interact with the surface 6, but the air flow will act to dissipate the by-products of the cold plasma after the cold plasma treatment has ended.

Alternatively, the controller 9 may be configured such that the air flow generator 8 generates an air flow during treatment, and continues to generate an air flow after t treatment has been completed. For example, the air flow generator 8 may be switched on at the same time as the cold plasma generator 14 and continue to generate an air flow after the treatment has been completed.

Alternatively, the controller 9 may be configured such that the air flow generator 8 generates an air flow before the cold plasma generator 14 has been switched on, and also after the treatment has been completed.

Alternatively, the controller 9 may be configured such that the air flow generator 8 starts to generate an air flow before the cold plasma generator has been switched on, continues to generate an air flow during treatment, and continues to generate an air flow after the treatment has been completed.

In each of these examples, the controller 9 may be configured to alter an operating characteristic of the air flow generator 8 when the treatment has been completed.

For example, the controller 9 may be configured to operate the air flow generator 8 such that a low rate of air flow is generated towards the surface 6 during treatment. In this way, during treatment the reactive species generated by the cold plasma are urged towards the surface 6 without being dispersed. Then, once the treatment has been completed, the controller 9 may be configured to operate the air flow generator 8 such that a higher rate of air flow is generated towards the surface 6, to dissipate by-products of the cold plasma.

In an alternative example, the controller 9 may be configured to operate the air flow generator 8 such that a low rate of air flow is generated towards the surface 6 during treatment. In this way, during treatment the reactive species generated by the cold plasma are urged towards the surface 6 without being dispersed. Then, once the treatment has been completed, the controller 9 may be configured to operate the air flow generator 8 such that an air flow is generated away from the surface 6 (i.e. the direction of the air flow generator 8 is reversed), to dissipate the by-products of the cold plasma. The rate of the air flow way from the surface 6 (after the treatment has been completed) may be higher than the rate of the air flow towards the surface 6 during treatment.

In some examples, the controller 9 is configured to determine when the treatment has been completed based on when the cold plasma generator 14 has been switched off.

In alternative examples, the cold plasma device 13 of any of the examples described with reference to FIG. 1 to FIG. 7, further comprises a sensor 18 that is adapted to detect when the cold plasma device 13 is positioned in contact with or proximate to the surface 6.

The sensor 18 may be a contact sensor or a proximity sensor, arranged to detect contact and/or proximity of the cold plasma device 13 to the surface 6. Examples of contact sensors include switches that are depressed on contact, electronic or optical contact sensors. An example of proximity sensor is a light source (e.g. an LED) and a sensor that measures the reflection of that light from the surface (more light is reflected the closer the surface is to the sensor). Alternatively, where the surface being treated has a temperature above ambient (e.g. skin), a proximity sensor may comprise an infrared temperature sensor or a capacitive sensor.

In some examples, as shown in FIG. 2 and FIG. 6, the sensor 18 may be disposed on the spacer element 5. However, it will be appreciated that the sensor 18 may alternatively be located elsewhere within the cold plasma device, particularly if the sensor 18 is a proximity sensor that can work at a distance from the surface 6. It will be appreciated that multiple contact and/or proximity sensors can be used on the same device.

Preferably, the sensor 18 is in communication with the controller 9, and the controller 9 is configured to control the cold plasma generator 14 and/or the air flow generator 8 in dependence on a signal from the sensor.

For example, when the sensor 18 detects that the cold plasma device 13 is positioned in contact with or adjacent to the surface 6 then the controller 9 may switch on the cold plasma generator 14 to start treating the surface 6. Additionally, the controller 9 may be configured to switch the air flow generator 8 on or off, or change its operating characteristics, when the sensor 18 detects that the cold plasma device 13 is positioned in contact with or adjacent the surface 6, depending on which of the above-described options is used.

Then, when the cold plasma device 13 is moved away (partially or completely) from the surface 6 the sensor 18 detects this and the controller 9 may be configured to switch off the cold plasma generator 14.

Further, the controller 9 may be configured to switch on, or change an operating characteristic, of the air flow generator 8 when the sensor 18 detects that the cold plasma device 13 is moved away (partially or completely) from the surface 6. In particular, the controller 9 may be configured to control operation of the air flow generator 8 to generate an air flow over the surface 6 after the sensor 18 detects that the treatment head 5 has been removed from the surface 6. That is, the sensor 18 is used to detect when the treatment has been completed, based on whether or not the treatment head 5 is in a position for treatment.

In an alternative example, the controller 9 is configured to control operation of the air flow generator 8 in dependence on whether the cold plasma device 14 is switched on or off.

In another example, the controller 9 is configured to control the air flow generator 8 based on a combination of whether the cold plasma generator 14 is switched on or off, and whether the sensor 18 detects that the treatment head 5 is in a position relative to the surface 6 for treating the surface 6.

Therefore, the controller 9 is able to determine when the treatment has been completed in three ways:
- when the treatment head 5 has been removed from the surface 6 (as detected by the sensor 18);
- when the cold plasma generator 14 has been switched off; or
- when the cold plasma generator 14 has been switched off and when the treatment head 5 has been removed from the surface 6.

In the embodiments described above the cold plasma device 13 is used to treat a surface 6. In specific examples, the cold plasma device 13 may be used to treat skin, for example human skin. In one example, the cold plasma device 13 is a deodorising device for treating an armpit to inactivate bacteria that give rise to body odour.

In other specific examples, the cold plasma device 13 may be for disinfection of articles, such as toothbrushes, shaver heads, medical equipment or similar. Alternatively, the cold plasma device 13 may be for disinfecting surfaces, for example in hospitals or in kitchens.

The above embodiments as described are only illustrative, and not intended to limit the technique approaches of the present invention. Although the present invention is described in details referring to the preferable embodiments, those skilled in the art will understand that the technique approaches of the present invention can be modified or equally displaced without departing from the spirit and scope of the technique approaches of the present invention, which will also fall into the protective scope of the claims of the present invention. In the claims, the word "comprising" does not exclude other elements or steps, and the indefinite article "a" or "an" does not exclude a plurality.

Any reference signs in the claims should not be construed as limiting the scope.

The invention claimed is:

1. A cold plasma device for treating a surface with cold plasma, the cold plasma device comprising:
   a housing;
   a cold plasma generator located in the housing and configured to generate cold plasma that produces reactive species for treating said surface;
   a treatment head connected to or integral with housing and positionable relative to said surface such that said reactive species are imparted toward said surface during treatment;

an air flow generator located in the housing and configured to generate an air flow through the housing and over said surface; and a controller located in the housing and configured to control operation of the air flow generator to generate the air flow over said surface after said treatment has been completed such that remaining by-products of the cold plasma are dissipated.

2. The cold plasma device of claim 1, wherein the controller is configured to control the air flow generator to generate the air flow over said surface only after said treatment has been completed.

3. The cold plasma device of claim 1, wherein the controller is configured to control the air flow generator to further generate the air flow over said surface during said treatment.

4. The cold plasma device of claim 3, wherein the controller is configured to alter an operating characteristic of the air flow generator after said treatment has been completed.

5. The cold plasma device of claim 4, wherein the controller is configured to increase a rate of the air flow by the air flow generator after said treatment has been completed.

6. The cold plasma device of claim 4, wherein the controller is configured to reverse a direction of the air flow generator after said treatment has been completed.

7. The cold plasma device of claim 1, further comprising a sensor adapted to detect when the treatment head is positioned in contact with or proximate to said surface, the controller being configured to switch on the cold plasma generator in response to a signal from the sensor.

8. The cold plasma device of claim 1, further comprising a sensor adapted to detect when the treatment head is positioned in contact with or proximate to said surface, the controller being configured to control operation of the air flow generator to generate the air flow over said surface after the sensor detects that the treatment head has been removed from said surface.

9. The cold plasma device of claim 1, wherein the controller is configured to control operation of the air flow generator to generate the air flow over said surface after said cold plasma generator has been switched off.

10. The cold plasma device of claim 1, wherein the air flow generator is adapted to generate a flow of air towards said surface.

11. The cold plasma device of claim 1, wherein the air flow generator is adapted to generate a flow of air away from said surface.

12. The cold plasma device of claim 1, wherein the cold plasma generator is mounted in the treatment head, and wherein the treatment head is adapted such that during treatment the cold plasma generator is proximate to, and spaced from, said surface.

13. The cold plasma device of claim 12, wherein the cold plasma generator comprises an aperture enabling the air flow generated by the air flow generator to pass through.

14. The cold plasma device of claim 12, further comprising a duct arranged to guide the air flow generated by the air flow generator, and wherein the duct bypasses the cold plasma generator and comprises an aperture disposed within the treatment head.

15. The cold plasma device of claim 1, wherein the controller is configured to control the air flow generator such that the air flow over said surface is maintained for a fixed time period after said treatment has been completed.

16. The cold plasma device of claim 1, wherein the air flow generator comprises a fan.

17. A cold plasma device for treating a surface with cold plasma, the cold plasma device comprising:

a cold plasma generator comprising a first electrode, a second electrode and a dielectric material separating the first electrode and the second electrode, the cold plasma generator being configured to generate cold plasma to produce reactive species from at least one gas provided between the first electrode and the second electrode in response to a voltage generated across the first electrode and the second electrode;

a spacer positionable between the cold plasma generator and the surface during a treatment, and arranged such that the reactive species are imparted toward the surface for treating the surface;

an air flow generator configured to generate an air flow, which passes over the surface;

a controller configured to control the air flow generator to generate the air flow after the treatment has been completed for dissipating remaining by-products of the cold plasma from the surface; and a housing in which the cold plasma generator, the air flow generator and the controller are located, wherein the housing is configured to act as a duct for conducting the air flow away from or toward the air flow generator.

18. The cold plasma device of claim 17, wherein the cold plasma generator defines a plurality of passages through which the air flow generated by the air flow generator to reach the surface.

19. The cold plasma device of claim 17, further comprising:

a duct configured to conduct the air flow between the air flow generator and the surface, bypassing the cold plasma generator.

20. The cold plasma device of claim 17, wherein the controller is further configured to control the air flow generator to generate the air flow at a first flow rate during the treatment, and to generate the air flow at a second flow rate, greater than the first flow rate, after the treatment has been completed.

* * * * *